US010100296B2

(12) United States Patent
Stelmasiak et al.

(10) Patent No.: US 10,100,296 B2
(45) Date of Patent: Oct. 16, 2018

(54) COMPOSITIONS FOR THE TREATMENT OF GLUTEN INTOLERANCE AND USES THEREOF

(75) Inventors: Teodor Stelmasiak, Maribyrnong (AU); Hugh James Beatty Cornell, Templestowe (AU)

(73) Assignee: Glutagen Pty Ltd, Victoria (AU)

( * ) Notice: Subject to any disclaimer, the term of this patent is extended or adjusted under 35 U.S.C. 154(b) by 1346 days.

(21) Appl. No.: 13/144,549

(22) PCT Filed: Jan. 6, 2010

(86) PCT No.: PCT/AU2010/000006
§ 371 (c)(1),
(2), (4) Date: Oct. 18, 2011

(87) PCT Pub. No.: WO2010/081185
PCT Pub. Date: Jul. 22, 2010

(65) Prior Publication Data
US 2012/0034299 A1    Feb. 9, 2012

(30) Foreign Application Priority Data

Jan. 15, 2009   (AU) ................. 2009900164

(51) Int. Cl.
  *C12N 9/64*    (2006.01)
  *A61K 38/48*   (2006.01)
  *A23L 29/00*   (2016.01)
  *A23L 33/105*  (2016.01)
  *A61K 48/00*   (2006.01)

(52) U.S. Cl.
  CPC ............ *C12N 9/6472* (2013.01); *A23L 29/06* (2016.08); *A23L 33/105* (2016.08); *A61K 38/4873* (2013.01); *A61K 48/00* (2013.01)

(58) Field of Classification Search
  None
  See application file for complete search history.

(56) References Cited

U.S. PATENT DOCUMENTS

2003/0026794 A1    2/2003  Fein
2004/0081648 A1*   4/2004  Afeyan et al. ............. 424/94.63

FOREIGN PATENT DOCUMENTS

AU    2008/100719 A4   9/2008
GB    2193720 A        2/1988
WO    WO-2003/100051 A1  12/2003
WO    WO-2004/033668 A2  4/2004

OTHER PUBLICATIONS

Cornell et al., Amino Acids, 2007, vol. 33, p. 43-49.*
Azarkan et al., Journal of Chromatography B, 790 (2003) 229-238.*
Shi et al., Journal of Integrative Plant Biology 2009, vol. 51 No. 1, p. 52-57.*
Messer et al., Gut, 1964, vol. 5, p. 295-303.*
Huet et al., Biochemical and Biophysical Research Communications, 2006, vol. 341, p. 620-626.*
Robinson et al., Biochemistry. Aug. 12, 1975;14(16):3695-700, Abstract Only.*
Messer et al., The Lancet, Nov. 6, 1976, p. 1022.*
Nitsawang et al., Enzyme and Microbial Technology, 2006, vol. 39, p. 1103-1107.*
Chaiwut et al., Chiang Mai. J. Sci., 2007, vol. 34, No. 1, p. 109-118.*
Brocklehurst et al "Fresh Non-Fruit Latex of *Carica papaya* Contains Papain, Multiple Forms of Chymopapain A and Papaya Proteinase Ω" Biochemical Journal Letters vol. 228, pp. 525-527, 1985.
Dekeyser et al "Kinetic Constants for the Hydrolysis of Aggrecan by the Papaya Proteinases and Their Relevance for Chemonucleolysis" Archives of Biochemistry and Biophsics vol. 320, pp. 375-379, 1995.

* cited by examiner

*Primary Examiner* — Kade Ariani
(74) *Attorney, Agent, or Firm* — Cesari and McKenna, LLP

(57) ABSTRACT

The present invention provides compositions for use in the prophylaxis or treatment of a condition arising from gluten intolerance, the compositions including at least partially purified caricain (or a biologically active fragment, analog or variant thereof) alone or in combination with other suitable enzymes including bromelain, and/or an intestinal extract, as herein described. The present invention also provides methods of using such compositions for the prophylaxis or treatment of a condition arising from gluten intolerance.

5 Claims, 4 Drawing Sheets

Specification includes a Sequence Listing.

Figure 1

MAMIPSISKLLFVAICLFVHMSVSFGDFSIVGYSQDDLTSTERLIQLFNSWMLNHNKFYE
NVDEKLYRFEIFKDNLNYIDETNKKNNSYWLGLNEFADLSNDEFNEKYVGSLIDATIEQ
SYDEEFINEDTVNLPENVDWRKKGAVTPVRHQGSCGSCWAFSAVATVEGINKIRTGKL
VELSEQELVDCERRSHGCKGGYPPYALEYVAKNGIHLRSKYPYKAKQGTCRAKQVGG
PIVKTSGVGRVQPNNEGNLLNAIAKQPVSVVVESKGRPFQLYKGGIFEGPCGTKVDHA
VTAVGYGKSGGKGYILIKNSWGTAWGEKGYIRIKRAPGNSPGVCGLYKSSYYPTKN

Figure 2

MAMIPSISKLLFVAICLFVHMSVSFGDFSIVGYSQDDLTSTERLIQLFNSWMLNHNKFYE

NVDEKLYRFEIFKDNLNYIDETNKKNNSYRLGLNEFADLSNDEFNEKYVGSLIDATIEQ

SYDEEFINEDIVNLPENVDWRKKGAVTPVRHQGSCGSCWAFSAVATVEGINKIRTGKL

VELSEQELVDCERRSHGCKGGYPPYALEYVAKNGIHLRSKYPYKAKQGTCRAKQVGG

PIVKTSGVGRVQPNNEGNLLNAIAKQPVSVVVESKGRPFQLYKGGIFEGPCGTKVDHA

VTAVGYGKSGGKGYILIKNSWGTAWGEKGYIRIKRAPGNSPGVCGLYKSSYYPIKNRD

NGRIQIRPSSQHLTSHE

Figure 3

```
  1 atggctatga taccttcaat ttcaaagttg cttttgttg caatatgtct ctttgttcat
 61 atgagtgtgt cctttggtga tttttctatc gtggggtatt cgcaagatga cttgacatct
121 actgagaggc ttattcagct ctttaactcg tggatgttga atcacaataa attttacgag
181 aatgttgatg agaaacttta cagatttgaa attttaagg acaatctaaa ctacattgac
241 gagacaaaca aaagaataa cagttattgg cttggattaa acgagtttgc tgatttaagc
301 aatgatgaat tcaatgagaa gtatgttggt tcccttattg atgcaacgat tgaacaatcc
361 tatgatgaag agtttattaa tgaagatact gtaaatttgc ccgagaatgt cgattggaga
421 aaaaaaggag ctgtcactcc cgtaagacat cagggttcat gcggtagttg ttgggcattc
481 tcggccgttg caactgtaga gggaataaat aagattagaa ctggaaaatt agtagaatta
541 tcagagcaag aacttgttga ctgtgaaaga cgtagccatg ggtgcaaagg aggttatccg
601 ccgtatgcac ttgaatatgt ggctaagaat ggtattcact tgagatcaaa gtacccatat
661 aaagcaaagc aagggacttg tcgagccaaa caagtgggag gtcccattgt gaaaacttct
721 ggggttggac gtgtgcaacc aaataatgaa gggaatctct taaatgcaat tgcaaagcaa
781 cctgtgagcg ttgtggttga atccaaggga agacctttcc aattgtataa aggggggaata
841 tttgaggggc catgcggaac caaagtagat catgcagtaa cagcagttgg ttatggaaaa
901 agtggaggca aaggttacat actcatcaag aattcatggg gtactgcatg gggtgagaaa
961 ggatatataa gaatcaaaag agcccctgga aactccccag gagtgtgtgg actttataaa
1021 agctcatact atcctactaa aaattga
```

Figure 4

```
   1 atggctatga taccttcaat ttcaaagttg ctctttgttg caatatgtct ctttgttcat
  61 atgagtgtgt cctttggcga tttttctatt gtggggtatt cgcaagatga cttgacatct
 121 accgagaggc ttattcagct ctttaactcg tggatgttga atcacaataa attttacgag
 181 aatgttgatg agaaacttta cagatttgaa attttaagg acaatctaaa ctacattgac
 241 gagacaaaca aaagaataa cagttatagg cttggattaa acgagtttgc tgatttaagc
 301 aatgatgaat tcaatgagaa gtatgttggt tcccttattg atgcaacaat tgaacaatcc
 361 tatgatgaag agtttattaa tgaagatatt gtaaatttgc ccgagaatgt cgattggaga
 421 aaaaaaggag ctgtcactcc cgtaagacat cagggttcat gcggtagttg ttgggcattc
 481 tcggccgttg caactgtaga gggaataaat aagattagaa ctggaaaatt agtagaatta
 541 tcagagcaag aacttgttga ctgtgaaaga cgtagccatg ggtgcaaagg aggttatccg
 601 ccgtatgcac ttgaatatgt ggctaagaat ggtattcact tgagatcaaa gtacccatat
 661 aaagcaaagc aagggacttg tcgagccaaa caagtgggag gtccgattgt gaaaacttct
 721 ggggttggac gtgtgcaacc aaataatgaa gggaatctct taaatgcaat tgcaaagcaa
 781 cctgtgagcg ttgtggttga atccaaggga agacctttcc aattgtataa aggggggaata
 841 tttgaggggc catgcggaac caaagtagat catgcagtaa cagcagttgg ttatggaaaa
 901 agtggaggca aaggttacat actcatcaag aattcatggg gtactgcatg gggtgagaaa
 961 ggatatataa gaatcaaaag agcccctgga aactccccag gagtgtgtgg actttataaa
1021 agctcatact atcctattaa aaatagagat aatggacgga tccagatccg cccatcatct
1081 caacacctca aagccatga atgaagctga
```

COMPOSITIONS FOR THE TREATMENT OF GLUTEN INTOLERANCE AND USES THEREOF

CROSS-REFERENCE TO RELATED APPLICATIONS

This application is the National Stage of International Application No. PCT/AU2010/000006, filed on Jan. 6, 2010, which claims the priority of Australian Patent Application No. 2009900164, filed on Jan. 15, 2009. The contents of both applications are hereby incorporated by reference in their entirety.

The present invention relates generally to compositions for the prophylaxis or therapy of conditions related to gluten intolerance, and uses thereof.

BACKGROUND

Gluten intolerance is found predominantly in areas where wheat is a major food source, (e.g., Europe, North America and Australia). In these areas, the incidence of the disease is about 1 per 100 head of population (DA Van Heel et al, Gut 2006; 55:1037-1046). The symptoms of this condition include abdominal pain, bloating and diarrhoea. In severe and long term cases, such as in coeliac disease, there are inflammatory changes to the intestinal mucosa, resulting in malabsorption of nutrients, fatigue, chronic diarrhoea, weight loss, abdominal distension, anaemia, increased tendency to haemorrhage, as well as increased risk of gastrointestinal malignancies, such as lymphoma and carcinoma.

The pathogenesis of gluten intolerance (or coeliac disease, coeliac sprue) appears to have both genetic and environmental factors. Whilst genetic predisposition is a major factor (about 10% of first degree relatives are affected), the fact that monozygotic twins have a concordance rate of only about 75% suggests that environment also plays a part in the development of the disease.

Patients with gluten intolerance characteristically have T cells present in the intestinal mucosa which recognize certain sequences present in toxic gluten peptides. Evidence suggests that these T cells play a crucial role in the immunopathogenesis of the disease by recognising peptides containing specific sequences of amino acids associated with toxicity. For instance, the proliferation of gliadin-specific HLA-DQ2-restricted T cell clones from the intestine of coeliac disease patients can be initiated in vitro by the addition of a water-soluble, partially digested form of gliadin to HLA-DQ2 carrying antigen-presenting cells.

A related disease associated with severe gluten intolerance is dermatitis herpetiformis, which presents as a chronic eruption characterized by clusters of intensely pruritic vesicles, papules, and urticaria-like lesions. Studies have shown that IgA deposits occur in almost all normal-appearing and perilesional skin. Asymptomatic gluten-sensitive enteropathy is found in 75 to 90% of patients and in some of their relatives. The onset of dermatitis herpetiformis is usually gradual, progressing to severe itching and burning of the affected surface. Moreover, scratching often obscures the primary lesions with eczematization of nearby skin, leading to an erroneous diagnosis of eczema.

Gluten is a protein fraction found, for example, in cereal dough, which can be subdivided into glutenins and prolamins. Prolamins may also be subclassified as gliadins, secalins, hordeins, and avenins from wheat, rye, barley and oat, respectively. Among gluten proteins with potential harmful effect to gluten intolerant patients are the storage proteins of wheat, species of which include Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi; etc. (see, for example, Colot, Genet Eng (NY) 12:225-41, 1990).

Gliadin is the 70% alcohol-soluble protein fraction of wheat gluten. Derived from wheat flour, gliadins can be classified into several groups according to their electrophoretic mobility, including α-type, β-type, γ-type and ω-type. Gliadins are typically rich in glutamine and proline, particularly in the N-terminal part. For example, the first 100 amino acids of α and γ-gliadins contain about 35% and about 20% of glutamine and proline residues, respectively. Different gliadins are present in each subcultivar of wheat, with variations in the amino acid sequences within each type. Gliadins are typically characterized by a molecular mass of around 30-50 kDalton and their insolubility in neutral aqueous solutions. Examples of gliadin sequences include but are not limited to wheat α-gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

It has been discovered that in gluten intolerant individuals, enzymes normally present in the small bowel that are necessary for the digestion of gluten are missing. Peptide fragments produced by incomplete digestion of grain protein are toxic to such individuals; the most toxic peptides being those derived from α-gliadin, or a similar protein called A-gliadin.

Serine-containing peptides, (containing PSQQ and possibly also QQQP motifs, as found in residues 11-19 of A-gliadin), appear to have a cytotoxic effect. Tyrosine-containing peptides, (containing QQPY and/or QPYP motifs, as found in residues 75-86 of A-gliadin), are associated with immunological activity through T-cell mediation and hence, toxicity.

Experiments indicate that active serine-containing peptides like 11-19 and active tyrosine-containing peptides like 75-86 are incompletely digested by mucosal enzymes in patients suffering from coeliac disease. The residual peptide sequences, such as 11-18 and 77-84, are still toxic, which suggests that the aetiology of coeliac disease is connected to defective mucosal digestion and that the pathogenesis of the disease results from the action of the undigested peptides on the mucosa. This may ultimately be due to deficiency in a single enzyme in coeliac disease patients, but at least two different types of peptide residues build up and cause damage to mucosal tissue.

At present, there is no effective therapy for treating the effects of gluten intolerance other than to impose a gluten-free diet on the patient. However, due to the number of food products containing either cereals comprising gluten, or gluten per se, this approach constitutes a severe restriction to the food choices available to a patient. Moreover, although gluten withdrawal has improved the prognosis of gluten intolerant patients, some people still die of the disease, presumably from lymphoreticular disease (especially intestinal lymphoma), particularly in those people who present with severe gluten intolerance at the outset. It appears that gluten withdrawal diminishes the risk of developing lymphoreticular disease, whilst apparent clinical remission is often associated with histologic relapse that is detected only by review biopsies or by an increased IgA class antiendomysial antibody (EMA) titre.

In view of the serious and widespread nature of gluten intolerance, improved methods of treating, preventing or ameliorating the effects of this condition are needed. Accordingly, it is an aspect of the present invention to overcome, or at least partly alleviate, some of the aforementioned problems of the art by providing improved compositions for preventing or treating conditions arising from gluten intolerance and methods for their use.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In one aspect of the present invention, there is provided a composition for the prophylaxis or treatment of a condition related to gluten intolerance, the composition including at least partially purified caricain, or a biologically active fragment, analogue or variant thereof.

In one embodiment, caricain is derived from *Carica papaya*.

In another embodiment, the caricain includes an amino acid sequence as shown in FIG. 1, or a biologically active fragment, analogue or variant thereof.

The composition according to the present invention may further include an animal intestinal enzyme extract, as herein described.

In another embodiment, the composition according to the present invention includes bromelain or a biologically active fragment, analogue or variant thereof.

The composition according to the present invention may be formulated as an enterically coated tablet or capsule.

In some embodiments of the present invention, the composition includes at least 15 mg of caricain, or a biologically active fragment, variant and analogue thereof.

In another aspect of the present invention, there is provided a composition for use in the prophylaxis or treatment of a condition related to gluten intolerance, the composition including a nucleic acid molecule that encodes recombinant caricain, or a biologically active fragment, analogue or variant thereof. In one embodiment, the nucleic acid molecule includes a nucleotide sequence as shown in FIG. 2, or a functional equivalent thereof. In another embodiment, the nucleic acid molecule encodes an amino acid sequence as shown in FIG. 1, or a biologically active fragment, analogue or variant thereof.

The composition according to the present invention may further include a nucleic acid molecule that is capable of expressing recombinant bromelain, or a biologically active fragment, analogue or variant thereof.

In another embodiment of the present invention, there is provided a composition for use in the prophylaxis or treatment of a condition related to gluten intolerance, wherein the composition includes a host cell that is capable of expressing recombinant caricain, or a biologically active fragment, analogue or variant thereof.

In yet another embodiment of the present invention, the composition includes a host cell that is capable of expressing recombinant bromelain or a biologically active fragment, analogue or variant thereof.

In another aspect of the present invention, there is provided a method for the prophylaxis or treatment of a condition related to gluten intolerance, the method including administering to a subject in need thereof a composition including at least partially purified caricain, or a biologically active fragment, analogue or variant thereof, as herein described. In some embodiments of the present invention, the composition includes at least 15 mg of caricain, or a biologically active fragment, variant and analogue thereof. In some embodiments of the present invention, the composition is administered to the subject in need thereof before a meal.

In one embodiment, the method according to the present invention includes administering to the subject in need thereof a composition including an intestinal extract.

In yet another embodiment, the method according to the present invention includes administering to the subject in need thereof bromelain or a biologically active fragment, analogue or variant thereof.

In another aspect of the present invention, there is provided a method for the prophylaxis or treatment of a condition arising from gluten intolerance, the method including administering to a subject in need thereof a nucleic acid molecule, wherein the nucleic acid molecule is capable of expressing in the subject recombinant caricain, or a biologically active fragment, analogue or variant thereof, as herein described.

In one embodiment, the method according to the present invention includes administering to the subject in need thereof a nucleic acid molecule that is capable of expressing in the subject recombinant bromelain, or a biologically active fragment, analogue or variant thereof.

It is yet another aspect of the present invention to provide a method of preparing an article of food derived from a gluten-containing material, the method including treating the article of food or the gluten-containing material with caricain, or a biologically active fragment, analogue or variant thereof, so as to reduce the amount of toxic gluten-derived oligopeptides present in the article of food. In one embodiment, the method according to the present invention may further include treating the article of food or the gluten-containing material with bromelain, or a biologically active fragment, analogue or variant thereof.

FIGURES

FIG. 1 illustrates the primary amino acid sequence of *Carica papaya* caricain (GenBank Accession No. X66060).

FIG. 2 illustrates the primary amino acid sequence of *Carica papaya* caricain (GenBank Accession No. X69877).

FIG. 3 illustrates the mRNA sequence of *Carica papaya* caricain (GenBank Accession No. X66060).

FIG. 4 illustrates the mRNA sequence of *Carica papaya* caricain (GenBank Accession No. X69877).

DETAILED DESCRIPTION OF THE INVENTION

Compositions

In one aspect of the present invention, there is provided a composition for the prophylaxis or treatment of a condition related to gluten intolerance, the composition including at least partially purified caricain, or a biologically active fragment, analogue or variant thereof.

It has been found that caricain is capable of modifying toxic oligopeptides that are produced following gluten ingestion to produce non-toxic peptides, thereby offering an improved method of preventing or at least partly alleviating their toxic effect in gluten intolerant individuals. Without being bound by theory, it is expected that the effect is dose-dependent of the enzyme quantity and the amount of ingested gluten.

As used herein, the term "caricain" (EC 3.4.22.30) refers to a cysteine protease typically found in the latex of plants such as *Carica papaya*. Other names by which caricain is known in the art include papaya protease omega, papaya endopeptidase III, papaya peptidase A, papaya peptidase II and papaya proteinase III. Caricain is a member of the papain superfamily and is homologous to other plant and animal cysteine proteases. Caricain is naturally expressed as an inactive zymogen called pro-caricain. The inactive form of the protease contains an inhibitory pro-region which consists of an additional 106 N-terminal amino acids. Studies have shown that the rate-limiting step in the in vitro activation of procaricain is the dissociation of the prodomain, which is then followed by proteolytic cleavage of the extended polypeptide chain of the proregion. The prodomain provides a stable scaffold which may facilitate the folding of the C-terminal lobe of procaricain (see Groves et al., 1996, *Structure*, 4(10):1193-1203). For the first time, the present inventors have identified caricain as a key enzyme in the conversion of toxic oligopeptides of gluten proteins such as wheat, to non-toxic fragments.

In one embodiment, caricain is derived from *Carica papaya* and was discovered by Schack in 1967 (Dubey K. at al. 2007, Papain-like proteases: Applications of their inhibitors; *African Journal of Biotechnology* 6 (9) 1077-1086).

In another embodiment, the caricain includes an amino acid sequence as shown in FIG. 1, or a biologically active fragment, analogue or variant thereof.

The composition according to the present invention may further include an intestinal enzyme extract, such as is described in international patent application PCT/AU03/00633 (publication no. WO 2003/100051; the contents of which are incorporated herein by reference). The present inventors have identified, for the first time, synergism in the combination of caricain and the intestinal enzyme extract described in WO 2003/100051.

At Least Partially Purified Caricain

In one embodiment of the present invention, caricain is at least partially purified from a natural source (e.g., papaya latex) in accordance with conventional methods known to the skilled addressee. In a certain embodiment of the present invention, caricain is at least partially purified from the latex of *Carica papaya* using any method known in the art, including, but not limited to, the methods described in Azarkan M. et al. ("Fractionation and purification of the enzymes stored in the latex of *Carica papaya*", *J Chromatogr B Analyt Technol Biomed Life Sci.* 2003 790(1-2): 229-38) and Buttle D. J. (Caricain In *Handbook of Proteolytic Enzymes*, 2 edition, p. 1130-1132, Elsevier, London).

Papaya, the fruit of the tree *Carica papaya*, in the genus *Carica*, is also known as mamaõ, tree melon, fruta bomba, lechosa or pawpaw. Methods useful for the isolation of caricain from a natural source such as papaya latex include, but are not limited to, solid-liquid extraction, liquid-liquid extraction, solid-phase extraction, membrane filtration, ultrafiltration, dialysis, electrophoresis, solvent concentration, centrifugation, ultracentrifugation, liquid or gas phase chromatography (including size exclusion chromatography, affinity chromatography, etc) with or without high pressure, lyophilisation, evaporation, precipitation with various "carriers" (e.g., antibodies), crystallization, and any combination thereof. The skilled addressee would understand how to use such options, in a sequential fashion, in order to enrich each successive fraction for caricain by following its activity throughout the purification procedure. The activity of the at least partially purified caricain can be measured using a variety of methods known to the skilled addressee, as herein described.

Solid-liquid extraction includes, but is not limited to, the use of various solvents, vortex shakers, ultrasounds and other means to enhance extraction, as well as recovery by filtration, centrifugation and related methods as described in the art (see, e.g., Cannell R J P, *Natural Products Isolation*, Humana Press, 1998). Examples of solvents that may be used include, but are not limited to, hydrocarbon solvents, chlorinated solvents, organic esters, organic ethers, alcohols, water, and combinations thereof.

Liquid-liquid extraction includes, but is not limited to, the use of solvents known in the art such as hydrocarbon solvents, chlorinated solvents, organic esters, organic ethers, alcohols, water, various aqueous solutions, and combinations thereof. The liquid-liquid extraction can be facilitated manually, or it can be automated (completely or in part), and the solvent can be removed and/or concentrated by standard techniques in the art.

Membrane, reverse osmosis and ultrafiltration include, but are not limited to, the use of various types of membranes known in the art, as well as the use of pressure, vacuum, centrifugal force, and/or other means that can be utilised in membrane and ultrafiltration processes.

Dialysis typically includes the use of membranes having a molecular weight cut-off that is selective for the removal of various constituents from the natural source so as to increase the relative purity of caricain in a sample. The present invention also encompassed the recovery of purified and/or fractionated extracts from either the dialysate or the retentate by various means known in the art including, but not limited to, lyophilization and crystallization.

Chromatography includes, but is not limited to, the use of regular column chromatography, flash chromatography, high performance liquid chromatography (HPLC), medium pressure liquid chromatography (MPLC), supercritical fluid chromatography (SFC), countercurrent chromatography (CCC), moving bed chromatography, simulated moving bed chromatography, expanded bed chromatography, and planar chromatography. Examples of sorbents that may be used in chromatography include, but are not limited to, silica gel, alumina, fluorisil, cellulose and modified cellulose, various modified silica gels, ion-exchange resins, size exclusion gels, chemically modified gels, and other sorbents known to those skilled in the art. The present invention also includes the use of two or more salt gradients to effect the fractionation and/or partial purification of caricain by chromatographic methods. When water or an aqueous phase is used, it may contain varying amounts of inorganic or organic salts, and/or the pH may be adjusted to different values with an acid or a base such that fractionation and/or purification is enhanced.

The process of at least partially purifying caricain from a natural source may also include the concentration of the purified or partially purified caricain by solvent removal of the original extract and/or fractionated extract, and/or purified extract. The techniques of solvent removal are known to those skilled in the art and include, but are not limited to, rotary evaporation, distillation (normal and reduced pressure), centrifugal vacuum evaporation (speed-vac), lyophilization and combinations thereof.

When referring to peptides, proteins and peptide analogs (e.g., caricain or bromelain) of the invention, the term "at least partially purified" typically means a composition which is partially to completely free of other components (e.g., other proteins, nucleic acids, lipids, carbohydrates) with which the peptides, proteins or analogs are associated in a non-purified, e.g., native state or environment. The at least partially purified peptides and proteins can generally be in a homogeneous or nearly homogenous state, although it can be either in a dry state or in an aqueous solution. Purity and homogeneity are typically determined using analytical chemistry techniques such as polyacrylamide gel electrophoresis or high performance liquid chromatography. In one embodiment, peptides such as caricain can be further purified using routine and well-known methods, such as those described herein.

In a certain embodiment of the present invention, the at least partially purified protein such as caricain can constitute at least about one or a few percent by weight of the total weight of the composition, for example, at least about five percent by weight of the total weight of the composition. In another embodiment, the at least partially purified caricain can constitute at least about ten percent by weight of the total weight of the composition. In another embodiment, the at least partially purified caricain constitutes at least about twenty percent by weight of the total weight of the composition. In another embodiment, the at least partially purified caricain can constitute at least about fifty percent by weight of the total weight of the composition. In a further embodiment, the at least partially purified caricain can constitute at least about eighty percent by weight of the total weight of the composition. In other embodiments, the at least partially purified caricain constitute at least about ninety percent or at least about ninety-five percent or more by weight of the total weight of the composition.

In other embodiments, the composition can be an oral composition that contains caricain at about 5% w/w to about 95% w/w, based on the total weight of the oral composition.
Assay for Caricain Activity Partially purified caricain can be tested for its ability to reduce the toxicity of toxic gluten peptides by any one or more of the procedures herein described. It will be understood by the skilled addressee that methods of isolating and purifying caricain from papaya latex, or from any other suitable source, will be such that at least some enzyme activity of the isolated peptidase is retained so as to provide for the prophylaxis or treatment of a condition arising from gluten intolerance. One skilled in the art would appreciate that there are numerous methods and techniques for measuring qualitatively and/or quantitatively the ability of the at least partially purified caricain to reduce the toxicity of toxic gluten peptides, either in vitro or in vivo, as herein described.

Caricain, as herein described, may be identified by its ability to modify a substrate to inactivate toxic gluten oligopeptides, where the substrate may include, but is not limited to, a gliadin, hordein, secalin or avenin protein. Toxic gliadin oligopeptides include peptides derived during normal human digestion of gliadins and related storage proteins, as herein described, from dietary cereals (e.g. wheat, rye, barley, and the like). Such oligopeptides are believed to act as antigens for T cells in patients suffering from a condition arising from gluten intolerance, such as Celiac Sprue. For binding to Class II MHC proteins, immunogenic peptides are usually from about 8 to 20 amino acids in length, more usually from about 10 to 18 amino acids. Such peptides may include QQPY or related tyrosine-containing motifs. Determination of whether an oligopeptide is immunogenic for a particular patient is readily determined by standard T cell activation and other assays known to those of skill in the art. The ability of caricain, or a biologically active fragment, analogue or variant thereof, as herein described, to inactivate a toxic gluten peptide can be determined by any methods known in the art, for example, by using a Rat Liver Lysosome (RLL) assay, as described, for example, in WO 2003/100051 and Cornell and Townley (1974; *Gut,* 15(11):862-869), both of which are incorporated herein by reference.

In a certain embodiment, the caricain according to the present invention is capable of modifying toxic peptides such as those containing PSQQ, QQQP and QQPY motifs, and the A-gliadin wheat peptides QNPSQQQPQ (residues 11-19), RPQQPYPQPQPQ (residues 75-86), LGQQQPFP-PQQPY (residues 31-43), PQPQPFPSQQPY (residues 44-55) and LGQGSFRPSQQN (residues 206-217).

The ability of caricain to modify a substrate can be determined, for example, by measuring the ability of an enzyme to increase the concentration of free $NH_2$-termini in a reaction mixture containing 1 mg/ml substrate and 10 mg/ml of caricain, incubated at 37° C. for 1 hour. Caricain according to the present invention will increase the concentration of the free amino termini under such conditions, usually by at least about 10%, more usually by at least about 25%, and preferably by at least about 50%. Caricain according to the present invention may also be capable of reducing the toxicity of oligopeptides greater than about 1000 Da in a 0.1 ml of 50 mg/ml substrate after a 2 hour incubation with 0.2 ml of 10 mg/ml of the peptidase by at least about 2-fold, usually by at least about 5-fold, and preferably by at least about 10-fold. The toxicity of such oligopeptides can be determined by methods known in the art, for example, by using a Rat Liver Lysosome (RLL) assay, as described, for example, in WO 2003/100051 and Cornell and Townley (1973); *Clin. Chim. Acta* 49: 181-188 both of which are incorporated herein by reference.

In one embodiment of the present invention, caricain will display detoxifying activity (as measured, e.g., by an RLL assay) of at least about 20%, optionally of at least about 50% or optionally of at least about 90% protection to the lysosomes.

In some embodiments of the present invention, the composition includes at least 15 mg of caricain, or a biologically active fragment, variant and analogue thereof.
Other Compositions In another embodiment of the invention, compositions of interest may include caricain in combination with other enzymes capable of inactivating toxic gluten oligopeptides, including, but not limited to bromelain and an intestinal extract, such as is described in international patent application PCT/AU03/00633 (publication no. WO 2003/100051, the contents of which are incorporated herein by reference).

It has been found by the present inventors that the combination of caricain with an intestinal enzyme extract (as described, e.g., in WO 2003/100051) produces a surprisingly synergistic effect on the cleavage of toxic gliadin oligopeptides, as demonstrated, for example, in a Rat Liver Lysosome Protection Assay.

Bromelain is a plant protease which is typically isolated from pineapple (*Ananas comosus*). It has an optimum pH range of 5 to 8 depending upon the substrate with broad specificity for peptide bonds. Bromelain may be purified from sources such as pineapple using any standard technique known in the art, including, but not limited to, the method of purification described by Yamada F. et al. ("Purification and characterization of a proteinase from pineapple fruit, fruit bromelain FA2"; *J Biochem* (Tokyo). 1976; 79(6): 1223-34). Isolated and purified bromelain is also available commercially.

Caricain has been found by the present inventors to elute with a high molecular weight fraction of papaya latex (Fraction 4 in the 30-35 KDa range; see Examples section), consistent with the sequence of its active form (Groves et al., 1996, *Structure*, vol 4:1193-1203). Further purification of Fraction 4 by HPLC on Biosep SEC S 2000 confirmed that the early high molecular weight portion of Fraction 4 contained caricain, glutamine cyclotransferase and chymopapain, but the latter two enzymes do not appear to be significant contributors to detoxification of gliadin. The applicant has shown that phenylmethyl sulfonyl fluoride (PMSF) does not significantly inhibit the action Fraction 4 on rat liver lysosomes at 6 mM concentration, confirming that the main enzymes present in this fraction were not serine proteases.

The intestinal extract, as herein described, may be derived from any portion of a gastrointestinal tract, including, but not limited to, the duodenum. The intestinal extract may be derived from any species, as long as it displays an ability to detoxify toxic gliadin peptides alone, or in a synergistic capacity with a caricain. In a certain embodiment of the present invention, the intestinal extract in derived from porcine intestine.

Other animal forms of these proteins may be used, or modified forms may be isolated from other commercially available sources.

The compositions of the present invention may also include other enzymes, such as (but not limited to) fungal proteases from *Aspergillus* spp. such as *Aspergillus oryzae* (e.g. Byun et al. (2001) *J. Agric. Food Chem.* 49, 2061-2063) and *Lactobacilli* spp. such as *Lactobacillus helveticus* (e.g. Vesanto et al., (1995) *Microbiol.* 141, 3067-3075), and *Lactococcus lactis* (Mayo et al., (1991) *Appl. Environ. Microbiol.* 57, 38-44).

Biologically Active Fragments, Variants and Analogues Thereof

As used herein and with reference to caricain, the term "biologically active fragment" typically refers to a fragment that retains its ability to detoxify gluten peptides, in vitro or in vivo.

Peptidase fragments of interest include, but are not limited to, fragments of at least about 20 contiguous amino acids, more usually at least about 50 contiguous amino acids, and may comprise 100 or more amino acids, up to the complete protein, and may extend further to include additional sequences. In each case, the key criterion is whether the fragment retains the ability to modify the toxic oligopeptides that contribute to a condition arising from gluten intolerance.

As used herein, the term "native" preferably refers to caricain having an amino acid sequence that occurs in nature (e.g., a natural protein). Such fragments may generally be identified using techniques well known to those skilled in the art in identifying peptidase activity, for example, as hereinbefore described.

As used herein and with reference to bromelain, the term "biologically active fragment" typically refers to a fragment of bromelain that retains its ability to contribute to the detoxification of gluten peptides in combination with caricain, or a biologically active fragment, analogue or variant thereof.

As used herein and with reference to caricain, the term "analogue" typically denotes a peptidase that has an amino acid sequence that is substantially identical to the amino acid sequence of the naturally occurring caricain. As used herein and with reference to bromelain, the term "analogue" typically denotes a peptidase that has an amino acid sequence that is substantially identical to the amino acid sequence of the respective naturally occurring enzyme.

The term "substantially identical", as used in regards to an analogue, typically denotes a substitution or addition of one or more amino acids such that the resulting analogue has at least some of the biological activity of the naturally occurring enzyme. Analogues may be naturally occurring, such as an allelic variant or an mRNA splice variant, or they may be constructed using synthetic or recombinant techniques available to one skilled in the art.

As used herein and with reference to caricain and bromelain, the term "variant" typically denotes an enzyme that exhibits an amino acid sequence that is at least 80% identical to the native enzyme. Also contemplated are embodiments in which a variant comprises an amino acid sequence that is at least 90% identical, optionally at least 95% identical, optionally at least 98% identical, optionally at least 99% identical, or optionally at least 99.9% identical to the native molecule. Percent identity may be determined by visual inspection and/or mathematical calculation by methods known to those skilled in the art. Variants may be naturally occurring, synthetic or recombinant.

In one embodiment of the present invention, a variant of caricain or bromelain includes an enzyme that is substantially homologous to the native form of the enzyme, but which has an amino acid sequence different from that of the native form because of one or more deletions, insertions or substitutions. Certain embodiments include amino acids that comprise from one to ten deletions, insertions or substitutions of amino acid residues when compared to a native sequence. A given sequence may be replaced, for example, by a residue having similar physiochemical characteristics. Examples of such conservative substitution of one aliphatic residue for another, such as Ile, Val, Leu or Ala for one another; substitution of one polar residue for another, such as between Lys and Arg, or Glu and Asp, or Gln and Asn; or substitutions of one aromatic residue for another, such as Phe, Trp or Tyr for one another. Other conservative substitutions, e.g., involving substitutions of entire regions having similar hydrophobicity characteristics, are well known in the art. Variants may also be generated by the truncation of a native peptidase amino acid. Further variants encompassed by the present invention include, but are not limited to, deglycosylated amino acids, or fragments thereof, or those amino acids demonstrating increased glycosylation when compared to the native enzyme.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan). Thus, an amino acid residue of caricain is preferably replaced with another amino acid residue from the same side chain family. In a preferred embodiment, mutations can be introduced randomly along all or part of the enzyme coding sequence, such as by saturation mutagenesis. The resultant mutants can be screened to identify variants that demonstrate at least some of the biological activity of the native enzyme. Following mutagenesis, the encoded protein can be expressed recombinantly and the activity of the enzyme can be determined by the methods described herein.

Also envisaged are modifications that do not alter the primary sequence of the native form of caricain or bromelain, including, but not limited to, chemical derivatization of proteins (e.g., acetylation or carboxylation), glycosylation (e.g., those made by modifying the glycosylation patterns of a protein during its synthesis and processing or in further processing steps), as well as sequences that have phosphorylated amino acid residues (e.g., phosphotyrosine, phosphoserine, or phosphothreonine).

Also useful in the practice of the present invention is caricain or bromelain that has been modified using molecular biological techniques and/or chemistry so as to improve their resistance to proteolytic degradation and/or to acidic conditions such as those found in the stomach, and to optimize solubility properties or to render them more suitable as a therapeutic agent. Analogs of such proteins include those containing residues other than naturally occurring L-amino acids (e.g., D-amino acids or non-naturally occurring synthetic amino acids).

The caricain according to the present invention may be prepared by in vitro synthesis using conventional methods as known in the art. Various commercial synthetic apparatuses are available, for example, automated synthesizers (e.g., CS936X Peptide Synthesizer, CSBio Company, Inc.). Using such synthesizers, a skilled person can readily substitute for the naturally occurring amino acids one or more unnatural amino acids. The particular sequence and the manner of preparation will be determined by convenience, economics, purity required, and the like. If desired, various groups can be introduced into the protein during synthesis that allow for linking to other molecules or to a surface. For example, cysteines can be used to make thioethers, histidines can be used for linking to a metal ion complex, carboxyl groups can be used for forming amides or esters, amino groups can be used for forming amides, and the like.

Nucleic Acid Molecules

In yet another aspect of the present invention, there is provided a composition for the prophylaxis or treatment of a condition arising from gluten intolerance, the composition including a nucleic acid molecule having a nucleic acid sequence that encodes caricain, or a biologically active fragment, analogue or variant thereof. The nucleic acid molecule should be capable of driving the expression of a recombinant analogue of caricain, including a biologically active fragment, analogue or variant thereof. For example, and without being bound by theory, the nucleic acid molecule may transfect a cell lining the gastrointestinal tract of a subject into whom it has been administered, where it becomes incorporated into the subject's genome. The incorporation of the nucleic acid molecule will then result in the expression of the recombinant caricain, or a biologically active fragment, analogue or variant thereof.

As used herein, the term "nucleic acid molecule" includes DNA molecules (e.g., a cDNA or genomic DNA) and RNA molecules (e.g., an mRNA) and analogs of the DNA or RNA generated, for example, by the use of nucleotide analogues. The nucleic acid molecule can be single-stranded or double-stranded, but preferably is double-stranded DNA. Encompassed by the present invention are naturally occurring and synthetic nucleic acid molecules, or combinations thereof, whose nucleic acid sequence encodes caricain, or a biologically active fragment, analogue or variant thereof, as hereinbefore described.

As used herein, a "naturally-occurring" nucleic acid molecule typically refers to an RNA or DNA molecule having a nucleotide sequence that occurs in nature (e.g., as found in a papaya plant).

As used herein, the terms "gene" and "recombinant gene" preferably refer to nucleic acid molecules which include an open reading frame encoding a peptidase as herein described, and can further include non-coding regulatory sequences, and introns.

For example, the nucleic acid molecule encoding caricain includes a nucleotide sequence which is about 65% to about 99% or more homologous to a nucleotide sequence encoding a naturally-occurring caricain. The nucleic acid molecule encoding caricain may be derived from any source, including, but not limited to papaya, whereas the analogues envisaged as being within the spirit of the present invention may be derived from non-plant species, including, but not limited to, human, porcine. ovine and bovine.

In a certain embodiment of the present invention, the nucleic acid molecule includes a nucleic acid sequence as shown in FIG. 2, or a functional equivalent thereof.

As used herein, the term "functional equivalent thereof" refers to a sequence that has an analogous function to the sequence of which it is a functional equivalent. By "analogous function" is meant that the sequences share a common function, for example, in encoding caricain, or a biologically active fragment, analogue or variant thereof. In some embodiments, a functionally equivalent sequence may exhibit sequence identity with the sequence of which it is a functional equivalent. The sequence identity between the functional equivalent and the sequence of which it is a functional equivalent may be at least 50% across the length of the functional equivalent, at least 60% across the length of the functional equivalent or greater than 70%, 80%, 85%, 90%, 95%, 96%, 97%, 98% or 99% across the length of the functional equivalent.

In another embodiment of the present invention, the nucleic acid molecule encodes an amino acid sequence as shown in FIG. 1, or a biologically active fragment, analogue or variant thereof, as herein described. The nucleic acid molecules of the invention, as herein described, can be inserted into vectors and used as gene therapy vectors.

In yet another embodiment of the present invention, there is provided a composition, as herein described, further including a nucleic acid molecule that encodes recombinant bromelain, or a biologically active fragment, analogue or variant thereof, as herein described.

Host Cells

In yet another aspect of the present invention, there is provided a composition for the prophylaxis or treatment of a condition related to gluten intolerance, the composition including a host cell, wherein the host cell is capable of expressing recombinant caricain, or a biologically active fragment, analogue or variant thereof, as herein described. In certain embodiments of the present invention, the host cell is a eukaryotic cell or cell line of any species selected from the group including embryonic stem cells, embryonic carcinoma cells, hematopoietic stem cells, hepatocytes, fibroblasts, myoblasts, keratinocytes, endothelial cells, bronchial epithelial cells and immune cells. The host cell may also be of a lower organism such as bacteria. In one embodiment, the host cell may be a microorganism that can colonise the gastrointestinal tract of the recipient, such as, but not limited to, *Lactobacillus* spp.

In another embodiment of the present invention, the host cell is a plant engineered to express recombinant caricain and/or bromelain, or biologically active fragments, analogues or variants thereof, as herein described. For example, the host cell may be an edible plant, wherein a subject in need thereof (e.g., a subject showing, or at risk of showing, symptoms of gluten intolerance) is able to ingest the edible plant, thereby administering a dose of the recombinant caricain and/or bromelain (or biologically active fragments, analogues or variants thereof, as herein described). As used herein, the term "plant" includes reference to whole plants, plant parts or organs (e.g., leaves, stems, roots, etc.), plant cells, seeds and progeny of same. The term "plant cell", as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include engineered cells, such as protoplasts, obtained from the aforementioned tissues. The class of plants which can be used in accordance with the present invention is generally as broad as the class of higher plants amenable to transformation techniques, including both monocotyledonous and dicotyledonous plants. Particularly preferred plants include maize, soybean, sunflower, sorghum, canola, alfalfa, cotton, rice, barley, and millet.

Any suitable method may be used to engineer a plant cell to express recombinant caricain and/or bromelain (or biologically active fragments, analogues or variants thereof, as herein described), including, but not limited to, the methods described in U.S. Pat. No. 6,977,325 (the contents of which are incorporated herein be reference).

The composition may further include a host cell that is capable of expressing recombinant bromelain, or a biologically active fragment, analogue or variant thereof, as herein described. For example, in a certain embodiment of the present invention, the composition includes a host cell that expresses recombinant caricain (or a biologically active fragment, analogue or variant thereof, as herein described) and recombinant bromelain (or a biologically active fragment, analogue or variant thereof, as herein described). In another embodiment, the composition of the present invention includes a first host cell that expresses recombinant caricain (or a biologically active fragment, analogue or variant thereof, as herein described) and a second host cell that expresses recombinant bromelain (or a biologically active fragment, analogue or variant thereof, as herein described).

Pharmaceutical Compositions

The compositions according to the present invention, as hereinbefore described, may be in the form of a pharmaceutical composition, in which the composition further includes a pharmaceutically acceptable carrier, excipient, diluent and/or adjuvant. Pharmaceutical compositions of the present invention may be employed alone or in conjunction with other compounds, such as therapeutic compounds.

As used herein, the phrase "pharmaceutically acceptable carrier" includes, but is not limited to, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Typically, the route of administration is parenteral, including oral (e.g., ingestion, inhalation) or rectal. Solutions or suspensions used for parenteral application can include one or more of the following components: a sterile diluent such as water for injection, saline solution, fixed oils, polyethylene glycols, glycerine, propylene glycol or other synthetic solvents; antibacterial agents such as methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Generally, the pharmaceutical composition is stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, or liquid polyetheylene glycol, and the like), and suitable mixtures thereof. The proper fluidity can be maintained, for example, by the use of a coating such as lecithin, by the maintenance of the required particle size in the case of a dispersion or by the use of surfactants. Prevention of the action of microorganisms can be achieved by incorporation of various antibacterial and antifungal agents, for example, parabens, chlorobutanol, phenol, ascorbic acid, thimerosal, and the like. In many cases, it will be preferable to include isotonic agents, for example, sugar, sodium chloride or polyalcohols such as mannitol, or sorbitol, in the composition.

Oral compositions generally comprise an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or modified corn starch; a lubricant such as magnesium stearate or other stearates; a glidant such as colloidal silicon dioxide; a sweetening agent such as sucrose or saccharin; or a flavouring agent such as peppermint, methyl salicylate, or orange flavouring.

In one embodiment, the compositions of the present invention are prepared with carriers that will protect the compositions according to the present invention against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers.

It is advantageous to formulate oral or parenteral compositions in dosage unit form for ease of administration and uniformity of dosage. "Dosage unit form", as used herein, refers to physically discrete units suited as unitary dosages for the subject to be treated; each unit containing a predetermined quantity of active compound calculated to produce the desired therapeutic effect in association with the required pharmaceutical carrier. The toxicity and therapeutic efficacy of such compounds can be determined by standard pharmaceutical procedures including in vitro assays, cell cultures or experimental animals, e.g., for determining the $LD_{50}$ (the dose lethal to 50% of the population) and the $ED_{50}$ (the dose therapeutically effective in 50% of the population) depending on the compound studied. The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the in vitro studies, cell culture assays and animal studies can be used in formulating a range of dosages for use in humans. The dosage lies preferably within a range of circulating concentrations that include the $ED_{50}$ with little or no toxicity. The dosage may vary within this range depending upon the dosage form employed and the route of administration utilized. The therapeutically effective dose of an enzyme can be estimated initially from in vitro assays. Such information can be used to more accurately determine useful doses in humans. In one embodiment of the present invention, the effective dose of caricain is at least about 0.1 mg per kg body weight taken with each meal for adults and typically half that dose for children.

Depending on the patient and condition being treated and on the administration route, caricain, or a biologically active fragment, variant and analogue thereof, may be administered in dosages of about 0.1 mg to about 500 mg/kg body weight per day, e.g. about 15 mg/day for an average person. For instance, a typical dose of caricain, or a biologically active fragment, analogue or variant thereof, in patients will be in at least about 1 mg/adult, more usually at least about 15 mg; and preferably at least about 50 mg; and preferably not more than about 500 mg. Dosages will be appropriately adjusted for pediatric formulation. In children the effective dose may be lower, for example at least about 0.1 mg, or 0.5 mg of caricain, or a biologically active fragment, variant and analogue thereof. In combination therapy involving, for example, caricain and intestinal prolidase, a comparable dose of the composition may be given; however, the ratio will be influenced by the relative stability of the composition toward gastric inactivation. The caricain may be present in the composition of the present invention as an at least partially purified extract, or as a synthesized pharmaceutically acceptable protein.

Those of skill in the art will readily appreciate that dose levels can vary as a function of the specific enzyme, the severity of the symptoms and the susceptibility of the subject to side effects. In some embodiments, dosages for a given enzyme are readily determinable by those of skill in the art by a variety of means. An exemplary means is to measure the biological activity of a given compound required to overcome the symptoms.

In some embodiments of the present invention, the composition of the present invention includes at least 15 mg caricain, or a biologically active fragment, variant and analogue thereof.

The skilled artisan will appreciate that certain factors may influence the dosage and timing required to effectively treat a subject, including the activity of the specific compound employed, the age, body weight, general health, gender, and diet of the subject, the time of administration, the route of administration, the rate of excretion, any drug combination, the degree of expression or activity to be modulated, sensitivity to gluten, previous treatments and other diseases present.

The pharmaceutical compositions can be included in a container, pack, or dispenser together with instructions for administration.

For oral preparations, the compositions according to the present invention can be used alone or in combination with appropriate additives to make tablets, powders, granules or capsules, for example, with conventional additives, such as lactose, mannitol, corn starch or potato starch; with binders, such as crystalline cellulose, cellulose variants, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the present invention, the oral formulations comprise enteric coatings, so that the active agent is delivered to the intestinal tract. Enteric formulations are often used to protect an active ingredient from the strongly acid contents of the stomach. Such formulations can be created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate, hydroxypropyl methylcellulose acetate succinate, methacrylate copolymers, cellulose acetate phthalate and acrylic coating systems such as Acryl-Ease (Colorcon).

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells (see, for example, Mathiowitz et al. (1997) *Nature* 386 (6623): 410-414. Drug delivery systems can also utilize a core of superporous hydrogels (SPH) and SPH composite (SPHC), as described by Dorkoosh et al. (2001) *J Control Release* 71 (3):307-18).

Methods of Prophylaxis or Treatment

In another aspect of the present invention, there is provided a method for the prophylaxis or treatment of a condition related to gluten intolerance, the method including administering to a subject in need thereof a composition according to the present invention, as herein described.

In some embodiments of the present invention, the method includes administering to the subject in need thereof at least 15 mg of caricain, or a biologically active fragment, variant and analogue thereof. In some embodiments of the present invention, the method includes administering to the subject in need thereof at least 15 mg of caricain, or a biologically active fragment, variant and analogue thereof before a meal, following a meal or with a meal.

The method of the present invention can be used for prophylaxis or safeguarding, as well as for therapeutic purposes. Accordingly, as used herein, the term "treatment" and the like refers to any diminution in the severity of a pre-existing disease, condition or symptom of gluten intolerance, particularly as measured by the severity of symptoms such as, but not limited to, fatigue, chronic diarrhoea, and malabsorption of nutrients, weight loss, abdominal distension and anaemia. As used herein, the term "prophylaxis" and the like refer to the prevention of a disease, condition or symptom of gluten intolerance. Other indices of gluten intolerance include, but are not limited to, the presence of antibodies specific for glutens, the presence of antibodies specific for tissue transglutaminase, the presence of pro-inflammatory T cells and cytokines, damage to the villous structure of the small intestine as evidenced by histological or other examination, enhanced intestinal permeability, and the like.

Subjects that can benefit from the methods of the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, for example, by HLA typing, by family history, by T cell assay, or by other means known to the skilled addressee.

In one embodiment of the present invention, the method of prophylaxis or treatment further includes administering to the subject in need thereof an effective dose of an at least partially purified caricain, or a biologically active fragment, analogue or variant thereof, as herein described.

In another embodiment of the present invention, the method of prophylaxis or treatment further includes administering to the subject in need thereof an effective dose of bromelain (or a biologically active fragment, analogue or variant thereof, as herein described), an intestinal extract (as hereinbefore described), or any combination thereof. Caricain may be administered together with bromelain and/or an intestinal extract or as separate dosages, as required.

In a further aspect of the present invention, the method of prophylaxis or treatment includes administering to a subject in need thereof a nucleic acid molecule including a nucleic acid sequence that encodes recombinant caricain or a biologically active fragment, analogue or variant thereof, as herein described. The methods of the present invention may further include administering to the subject a nucleic acid molecule including a nucleic acid sequence that encodes recombinant bromelain (or a biologically active fragment, analogue or variant thereof, as herein described).

In yet another aspect of the present invention, the method of prophylaxis or treatment includes administering to a subject in need thereof a host cell that is capable of expressing in the subject a recombinant caricain, or an analogue or variant thereof, as herein described. The methods of the present invention may further include administering to the subject a host cell that is capable of expressing recombinant bromelain (or a biologically active fragment, analogue or variant thereof, as herein described).

The methods according to the present invention may also be performed in combination with other modalities, including, but not limited to, administering to a subject in need thereof, an inhibitor of tissue transglutaminase, an anti-inflammatory agent, an anti-ulcer agent, a mast cell-stabilizing agents, and/or and an—allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

Various methods for administration may be employed, preferably using oral administration, for example with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

The therapeutic effect can be measured in terms of clinical outcome or can be determined by immunological or biochemical tests. Suppression of the deleterious T-cell activity can be measured by enumeration of reactive Th1 cells, by measuring the release of cytokines at the sites of lesions, or using other assays for the presence of autoimmune T cells known in the art. Alternatively, one can look for a reduction in severity of the symptoms of the disease.

Preparation of Food Articles

In another aspect of the present invention, there is provided a method of preparing an article of food derived from a gluten-containing material, the method including treating the article of food or the gluten-containing material with caricain, or a biologically active fragment, analogue or variant thereof, so as to reduce the amount of toxic gluten-derived oligopeptides present in the article of food.

In yet another aspect of the present invention, the method further includes treating the article of food or the gluten-containing material with bromelain (or a biologically active fragment, analogue or variant thereof, as herein described).

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention before the priority date of each claim of this application.

Finally it is to be understood that various other modifications and/or alterations may be made without departing from the spirit of the present invention as outlined herein.

Compositions and their use in the prophylaxis or treatment of conditions arising from gluten intolerance according to certain embodiments of the present invention will now be described in the following examples. It should be understood, however, that the following description is illustrative only and should not be taken in any way as a restriction on the generality of the invention described above.

EXAMPLES

Materials

Crude caricain was extracted (see Example 2) from dry Papaya latex (Enzyme Solutions). Papaya latex is a food grade mix of proteolytic enzymes isolated from papaya fruit. In two Rat Liver Lysosome (RLL) assays, crude caricain offered good protection of approximately 92%-94% at a concentration of about 10 mg/ml, using the normal amount of gliadin digest which is 5 mg for the assay.

The Rat Liver Lysosome (RLL) assay, as described, for example, in Cornell and Townley (1973; *Clinica Chimica Acta* 49:181-188) and Cornell and Townley (1974; *Gut*, 15(11):862-869), is based on the fact that a peptic-tryptic-pancreatinic digest of wheat gliadin disrupts rat liver lysosomes, causing a reduction in optical density (at 400 nm) of a suspension of these organelles. This is evidence of a cytotoxic reaction by the peptides present in the digest. However, if the enzyme extract is pre-incubated with the toxic gliadin digest for two hours, the change in optical density is much less after incubation with the lysosomes. By comparing a control (no toxic digest), a toxic sample (lysosomes incubated with a toxic digest of gliadin) and an extract treated sample (toxic digest of gliadin pre-incubated with enzyme extract prior to addition of lysosomes), the extent of protection can be determined. A protection index (P.I.) can be calculated from:

$$P.I.(\%) = \frac{\% \text{ reduction toxic sample} - \% \text{ reduction extract treated sample}}{\% \text{ reduction toxic sample}} \times 100$$

Example 1: Fractionation Experiments

To characterise caricain further, papaya latex was fractionated on an ion-exchange Carboxymethyl (CM) Sephadex C-50 column and on a size exclusion Sephacryl S-300 column.

The ion-exchange column (3.2×20 cm) was equilibrated with 0.02M phosphate buffer pH4.6 and 2 g of the crude papain applied in the starting buffer (30 ml). After the unabsorbed fraction was obtained, other fractions were eluted by increasing the pH by application of a 0.05 M phosphate buffer of pH6.8 and then by application of salt containing buffers of the same pH but containing 0.1M, 0.3M and 0.7M sodium chloride. The fractions were dialysed against distilled water and freeze-dried. They were then assayed using the RLL assay at a concentration of 10 mg/ml. The results are shown in Table 1 below:

TABLE 1

| Ion exchange chromatography | | | |
|---|---|---|---|
| Fraction | Yield % | Elution conditions | Protection Index (%) |
| 1 | 9.4 | Unabsorbed | 40 |
| 2 | 2.0 | change of pH | 53 |
| 3 | 20.0 | 0.1-0.3M NaCl | 70 |
| 4 | 15.0 | 0.7M NaCl | 84 |

The fractions collected from both the ion-exchange chromatography and the size exclusion chromatography were subsequently tested by both an RLL assay (as herein described, for example, by reference to WO 2003/100051 and Cornell and Townley (1973; *Clinica Chimica Acta* 49:181-188) the contents of which are incorporated herein by reference) and a PEP assay (as described, for example, Marti et al. Prolyl endopeptidase-mediated destruction of T cell epitopes in whole gluten: chemical and immunological characterization. *J Pharmacol Exp Ther.* 2005, 312(1):19-26; the contents of which are incorporated herein by reference) to characterise the active fractions of papaya latex. The PEP assay uses Z-glycylproline-4-nitro-anilide as substrate to measure the rate of attack on the C-terminal side of the proline residue.

The size exclusion Sephacryl S-300 column (88×2.2 cm) was equilibrated in pH 5.2 phosphate buffered saline and a sample of 1.2 g papaya latex in the buffer (10 ml) was applied carefully before continuing elution at the rate of 30 ml/hour. Fractions of 15 ml were collected, adjusted to pH 7.5 with 1M sodium hydroxide and assayed directly using 0.2 ml aliquots of each fraction. The results obtained are shown in Table 2.

TABLE 2

| Sephacryl S300 fractions tested by RLL assay: | |
|---|---|
| Sample | Protection Index (%) |
| Fraction 1 | 8 |
| Fraction 2 | 1 |
| Fraction 3 | 8 |
| Fraction 4 | 58 |
| Fraction 5 | 64 |
| Fraction 6 | 99 |
| Fraction 7 | 100 |
| Fraction 8 | 75 |
| Fraction 9 | 29 |
| Fraction 10 | 19 |

As illustrated in Table 2, above, fractions 6 and 7 offered the highest protection value and corresponded to proteins of approximately 30,000 Daltons MW. Fraction 5 contained the largest amount of prolyl endopeptidase (PEP) while Fraction 8 had the largest amount of proteases, as measured by the Benzoyl-arginine ethyl ester (BAEE) assay (see, for example, Arnon R. (1970) *Methods in Enzymology*, XIX, 226-228; the contents of which are incorporated herein by reference). These latter enzymes are normally reported as having molecular weight of about 23,000 Daltons.

Example 2: Synergistic Effect of Plant/Animal Derived Enzymes

A pig intestinal enzyme extract (as described, for example, in WO 2003/100051) was combined with a crude caricain preparation to assess whether there is a synergistic effect on their ability to detoxify toxic gluten peptides, as determined using the RRL assay, as hereinbefore described. Crude caricain was prepared by dissolving papaya latex extract in water, adjusting the concentration of ammonium sulphate to 60%, collecting the resulting precipitate by filtration, dialysing it and freeze-drying. This material was further enriched by chromatography on CM Sephadex using phosphate buffers with elution of the crude QC with 0.7 M sodium chloride, followed by dialysis and freeze-drying. The enzyme preparations were assayed using the RLL assay at a concentration of 6 mg/ml.

| | Pig intestinal extract (6 mg/ml) | Crude Caricain (6 mg/ml) | Combination (1:1) (6 mg/ml) |
|---|---|---|---|
| Protection Index (%) | 61 | 71 | 92* |

*This is about the same protection offered by 10 mg/ml of crude papain alone.

Example 3: Heat and Acid Resistance

Caricain has been shown to retain around 70% activity of its activity after exposure to heat or an acidic environment. For instance, the applicant has shown that caricain is highly resistant to heat through their observation that Fraction 4 from CM Sephadex chromatography retained about 80% of its activity after heating to 85° C. Furthermore, when Fraction 4 was treated with 0.05M hydrochloric acid for 15 hours, it retained about 70% of its activity, demonstrating that caricain is also acid resistant.

Example 4: Proteomics Analysis

The applicant has shown through mass spectrometry analysis that caricain as a major protein in Fraction 4 referred to in Example 1 (Table 1) above.

| Protein identified | Number of peptides identified |
|---|---|
| Caricain precursor (EC 3.4.22.30) | 17 (38% coverage) |
| Chymopapain precursor (EC 3.4.22.6) | 6 (18% coverage) |
| Glutamine cyclotransferase precursor (EC 2.3.2.5) | 2 (7% coverage) |

The proteomics analysis was performed by the Joint Proteomics Services Facility at the Ludwig Institute for Cancer Research and The Walter and Eliza Hall Institute for Medical Research (Melbourne, Australia) using the following parameters:

| For publication of these results, the following information is required by journals: | |
|---|---|
| Information on MS/MS database search | |
| Peaklist generating software | extract_msn (Version 2.0, Thermo Fisher Scientific) |
| Parameters used | Minimum mass m/z 700, Maximum mass m/z 5000. Grouping tolerance, 1.5. Intermediate scans, 1. Minimum scans per group, 1. Precursor charge, AUTO Minimum peaks in .DTA, 10. |
| Search engine | Mascot algorithm (Version 2.1.04, Matrix Science) Search Parameters |
| Enzyme specificity considered | Semi-trypsin. Considers all tryptic peptides as well as those that show tryptic specificity (KR) at one terminus, but where the other terminus may be a non-tryptic cleavage. |
| # of missed cleavages permitted | 3. Considers partial fragments where the digest was not complete. |
| Fixed Modifications | +58 Da for Carboxymethyl (Cysteine) if iodoacetic was used for the alkylation process. +57 Da for Carbamidomethyl (Cysteine) if iodoacetamide was used for the alkylation process. |
| Variable Modifications. | +42 Da for Acetylation (N-terminus) and +16 Da for Oxidation (Methionine). |
| Mass tolerance for precursor ions | For LC-ESI Ion Trap MS data, +/− 2.0 Da. |
| Mass tolerance for fragment ions | For LC-ESI Ion Trap MS/MS data, +/− 0.5 Da. |
| Database searched | LudwigNR (Version Q1 2007). The latest protein nonredundent database produced by the Office of Information Technology of the Ludwig Institute for Cancer Research and obtained from the Swiss Institute of Bioinformatics (Moritz et al, *Anal. Chem.* 2004 76: 4811-24). |
| Species restriction | None. |
| # protein entries actually searched | All LudwigNR proteins (i.e., currently over 4 million proteins). |

Example 5: Proteolytic Activity of Purified Caricain

A sample of purified caricain was supplied by The Free University of Brussels, Belgium (courtesy of Professor Yvan Looze; see Azarkan M et al., "Fractionation and purification of the enzymes stored in the latex of *Carica papaya*". *J Chromatogr B Analyt Technol Biomed Life Sci* (2003) 790: 229-238). The applicant has shown that this sample of purified caricain was highly active in the Rat Liver Lysosome (RLL) Assay, as herein described, as compared to crude caricain.

Calculations:
Protection offered against gliadin in RLL Assay=32.3%
Specific activity=32.3/0.0043=7512 (where 0.0043 is the number of milligrams in the assay; i.e., 4.3 micrograms).
The specific activity of crude caricain was 40. Therefore, the fold-purification achieved was =7512/40=188 (being the ratio of specific activities).

Thus, the activity of the purified caricain was approximately 190 times that of crude caricain and was active even at levels as low as 4 micrograms in the RLL Assay. The results show that caricain contributes most to the detoxification of gliadin in these studies.

Example 6: Use of Caricain Extract in the Treatment of Symptoms Associated with Gluten Intolerance and Coeliac Disease A male of 45 years of age diagnosed with coeliac disease by biopsy was treated for his symptoms by taking tablets of caricain extract for a period of six weeks during which time he took one tablet (15 mg of caricain per tablet) at the start of each meal. The patient kept a daily record of all symptoms and graded them according to severity (0=no symptoms; 3=mild symptoms; 6=moderate symptoms). These results were compared against those from a six week period before the trial period during which time the patient recorded his symptoms in the same way.

The results showed a reduction in severity from 307 symptom points prior to the commencement of treatment to 86 symptom points (72% reduction) at the conclusion of treatment. Apart from the large reduction in symptom severity, the patient also experienced symptom-free days and responded that the tablets took the worry out of dining out. Exposure to gluten changed former episodes of diarrhoea to episodes of slight nausea when the tablets were used.

Example 7: Use of Caricain Extract in the Treatment of Symptoms Associated with Gluten Intolerance and Dermatitis Herpatiformis (DH)

A 48 year old male patient diagnosed with DH by biopsy was exposed for 7 days to a diet comprising breakfast cereal and toast and a lunch inclusive of a sandwich until he developed a moderately painful itch. After allowing three weeks for the itch to subside, the patient was exposed to the same diet for 7 days during which time he was also treated with a caricain extract in tablet form (15 mg of caricain per tablet), taken with each meal of breakfast and lunch. The patient noted that only a few mild itches developed while he was taking the caricain extract tablets and commented that they were most useful in alleviating the symptoms of his disease. From experience, he had noted that any further gluten challenge without the tablets would soon have produced a painful rash, whereas, on the caricain extract tablets, the mild and less frequent itch was considered less likely to develop to the stage of becoming a painful rash. The results demonstrated that sufferers of DH are likely to find that treatment with caricain can provide a safeguard against accidental ingestion of gluten or to help them tolerate small amounts of gluten without developing severe symptoms.

Future patent applications may be filed on the basis of or claiming priority from the present application. It is to be understood that the following claims are not intended to limit the scope of what may be claimed in any such future applications. Features may be added to or omitted from the claims at a later date so as to further define or re-define the invention or inventions.

The invention claimed is:

1. A method for treating gluten intolerance, the method comprising administering to a subject in need thereof an oral composition that contains caricain at about 5% w/w to about 95% w/w, based on the total weight of the oral composition.

2. The method according to claim 1, wherein the caricain is derived from *Carica papaya*.

3. The method according to claim 1, wherein the caricain has an amino acid sequence as shown in FIG. 1 or 2.

4. The method according to claim 1, wherein the composition is in the form of an enterically coated tablet or capsule.

5. The method according to claim 1, wherein the composition contains at least 15 mg of caricain.

* * * * *

SEQUENCE LISTING

<160> NUMBER OF SEQ ID NOS: 13

<210> SEQ ID NO 1
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 1

Pro Ser Gln Gln
1

<210> SEQ ID NO 2
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 2

Gln Gln Gln Pro
1

<210> SEQ ID NO 3
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 3

Gln Gln Pro Tyr
1

<210> SEQ ID NO 4
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 4

Gln Pro Tyr Pro
1

<210> SEQ ID NO 5
<211> LENGTH: 348
<212> TYPE: PRT
<213> ORGANISM: Carica papaya

<400> SEQUENCE: 5

Met Ala Met Ile Pro Ser Ile Ser Lys Leu Leu Phe Val Ala Ile Cys
1               5                   10                  15

Leu Phe Val His Met Ser Val Ser Phe Gly Asp Phe Ser Ile Val Gly
                20                  25                  30

Tyr Ser Gln Asp Asp Leu Thr Ser Thr Glu Arg Leu Ile Gln Leu Phe
            35                  40                  45

Asn Ser Trp Met Leu Asn His Asn Lys Phe Tyr Glu Asn Val Asp Glu
        50                  55                  60

Lys Leu Tyr Arg Phe Glu Ile Phe Lys Asp Asn Leu Asn Tyr Ile Asp
65                  70                  75                  80

Glu Thr Asn Lys Lys Asn Asn Ser Tyr Trp Leu Gly Leu Asn Glu Phe
                85                  90                  95

Ala Asp Leu Ser Asn Asp Glu Phe Asn Glu Lys Tyr Val Gly Ser Leu
            100                 105                 110

Ile Asp Ala Thr Ile Glu Gln Ser Tyr Asp Glu Glu Phe Ile Asn Glu
            115                 120                 125

Asp Thr Val Asn Leu Pro Glu Asn Val Asp Trp Arg Lys Lys Gly Ala
    130                 135                 140

Val Thr Pro Val Arg His Gln Gly Ser Cys Gly Ser Cys Trp Ala Phe
145                 150                 155                 160

Ser Ala Val Ala Thr Val Glu Gly Ile Asn Lys Ile Arg Thr Gly Lys
                165                 170                 175

Leu Val Glu Leu Ser Glu Gln Glu Leu Val Asp Cys Glu Arg Arg Ser
            180                 185                 190

His Gly Cys Lys Gly Gly Tyr Pro Pro Tyr Ala Leu Glu Tyr Val Ala
        195                 200                 205

Lys Asn Gly Ile His Leu Arg Ser Lys Tyr Pro Tyr Lys Ala Lys Gln
    210                 215                 220

Gly Thr Cys Arg Ala Lys Gln Val Gly Gly Pro Ile Val Lys Thr Ser
225                 230                 235                 240

Gly Val Gly Arg Val Gln Pro Asn Asn Glu Gly Asn Leu Leu Asn Ala
                245                 250                 255

Ile Ala Lys Gln Pro Val Ser Val Val Glu Ser Lys Gly Arg Pro
            260                 265                 270

Phe Gln Leu Tyr Lys Gly Gly Ile Phe Glu Gly Pro Cys Gly Thr Lys
        275                 280                 285

Val Asp His Ala Val Thr Ala Val Gly Tyr Gly Lys Ser Gly Gly Lys
    290                 295                 300

Gly Tyr Ile Leu Ile Lys Asn Ser Trp Gly Thr Ala Trp Gly Glu Lys
305                 310                 315                 320

Gly Tyr Ile Arg Ile Lys Arg Ala Pro Gly Asn Ser Pro Gly Val Cys
                325                 330                 335

Gly Leu Tyr Lys Ser Ser Tyr Pro Thr Lys Asn
            340                 345

<210> SEQ ID NO 6
<211> LENGTH: 367
<212> TYPE: PRT
<213> ORGANISM: Carica papaya

<400> SEQUENCE: 6

Met Ala Met Ile Pro Ser Ile Ser Lys Leu Leu Phe Val Ala Ile Cys
1               5                   10                  15

Leu Phe Val His Met Ser Val Ser Phe Gly Asp Phe Ser Ile Val Gly
            20                  25                  30

Tyr Ser Gln Asp Asp Leu Thr Ser Thr Glu Arg Leu Ile Gln Leu Phe
        35                  40                  45

Asn Ser Trp Met Leu Asn His Asn Lys Phe Tyr Glu Asn Val Asp Glu
    50                  55                  60

Lys Leu Tyr Arg Phe Glu Ile Phe Lys Asp Asn Leu Asn Tyr Ile Asp
65                  70                  75                  80

Glu Thr Asn Lys Lys Asn Asn Ser Tyr Arg Leu Gly Leu Asn Glu Phe
                85                  90                  95

Ala Asp Leu Ser Asn Asp Glu Phe Asn Glu Lys Tyr Val Gly Ser Leu
            100                 105                 110

Ile Asp Ala Thr Ile Glu Gln Ser Tyr Asp Glu Glu Phe Ile Asn Glu

```
            115                 120                 125
Asp Ile Val Asn Leu Pro Glu Asn Val Asp Trp Arg Lys Lys Gly Ala
    130                 135                 140

Val Thr Pro Val Arg His Gln Gly Ser Cys Gly Ser Cys Trp Ala Phe
145                 150                 155                 160

Ser Ala Val Ala Thr Val Glu Gly Ile Asn Lys Ile Arg Thr Gly Lys
                165                 170                 175

Leu Val Glu Leu Ser Glu Gln Glu Leu Val Asp Cys Glu Arg Arg Ser
            180                 185                 190

His Gly Cys Lys Gly Gly Tyr Pro Pro Tyr Ala Leu Glu Tyr Val Ala
        195                 200                 205

Lys Asn Gly Ile His Leu Arg Ser Lys Tyr Pro Tyr Lys Ala Lys Gln
    210                 215                 220

Gly Thr Cys Arg Ala Lys Gln Val Gly Gly Pro Ile Val Lys Thr Ser
225                 230                 235                 240

Gly Val Gly Arg Val Gln Pro Asn Asn Glu Gly Asn Leu Leu Asn Ala
                245                 250                 255

Ile Ala Lys Gln Pro Val Ser Val Val Glu Ser Lys Gly Arg Pro
            260                 265                 270

Phe Gln Leu Tyr Lys Gly Gly Ile Phe Glu Gly Pro Cys Gly Thr Lys
        275                 280                 285

Val Asp His Ala Val Thr Ala Val Gly Tyr Gly Lys Ser Gly Gly Lys
    290                 295                 300

Gly Tyr Ile Leu Ile Lys Asn Ser Trp Gly Thr Ala Trp Gly Glu Lys
305                 310                 315                 320

Gly Tyr Ile Arg Ile Lys Arg Ala Pro Gly Asn Ser Pro Gly Val Cys
                325                 330                 335

Gly Leu Tyr Lys Ser Ser Tyr Tyr Pro Ile Lys Asn Arg Asp Asn Gly
            340                 345                 350

Arg Ile Gln Ile Arg Pro Ser Ser Gln His Leu Thr Ser His Glu
        355                 360                 365

<210> SEQ ID NO 7
<211> LENGTH: 1047
<212> TYPE: DNA
<213> ORGANISM: Carica papaya

<400> SEQUENCE: 7
atggctatga taccttcaat ttcaaagttg cttttttgttg caatatgtct ctttgttcat      60
atgagtgtgt cctttggtga tttttctatc gtggggtatt cgcaagatga cttgacatct     120
actgagaggc ttattcagct cttttaactcg tggatgttga atcacaataa attttacgag     180
aatgttgatg agaaacttta cagatttgaa atttttaagg acaatctaaa ctacattgac     240
gagacaaaca aaaagaataa cagttattgg cttggattaa acgagtttgc tgatttaagc     300
aatgatgaat caatgagaa gtatgttggt tcccttattg atgcaacgat tgaacaatcc     360
tatgatgaag agtttattaa tgaagatact gtaaatttgc ccgagaatgt cgattggaga     420
aaaaaaggag ctgtcactcc cgtaagacat cagggttcat gcggtagttg ttgggcattc     480
tcggccgttg caactgtaga gggaataaat aagattagaa ctgaaaaatt agtagaatta     540
tcagagcaag aacttgttga ctgtgaaaga cgtagccatg gtgcaaagg aggttatccg     600 ccgtatgcac ttgaatatgt ggctaagaat ggtattcact tgagatcaaa gtacccatat     660
aaagcaaagc aagggacttg tcgagccaaa caagtgggag gtcccattgt gaaaacttct     720
```

```
ggggttggac gtgtgcaacc aaataatgaa gggaatctct taaatgcaat tgcaaagcaa    780
cctgtgagcg ttgtggttga atccaaggga agacctttcc aattgtataa aggggggaata   840 tttgaggggc catgcggaac caaagtagat catgcagtaa cagcagttgg ttatggaaaa    900
agtggaggca aaggttacat actcatcaag aattcatggg gtactgcatg gggtgagaaa    960
ggatatataa gaatcaaaag agcccctgga aactccccag gagtgtgtgg actttataaa   1020
agctcatact atcctactaa aaattga                                       1047
```

<210> SEQ ID NO 8
<211> LENGTH: 1110
<212> TYPE: DNA
<213> ORGANISM: Carica papaya

<400> SEQUENCE: 8

```
atggctatga taccttcaat ttcaaagttg ctctttgttg caatatgtct ctttgttcat     60
atgagtgtgt cctttggcga tttttctatt gtggggtatt cgcaagatga cttgacatct    120
accgagaggc ttattcagct cttttaactcg tggatgttga atcacaataa attttacgag   180
aatgttgatg agaaacttta cagatttgaa atttttaagg acaatctaaa ctacattgac    240
gagacaaaca aaaagaataa cagttatagg cttggattaa acgagtttgc tgatttaagc    300
aatgatgaat caatgagaa gtatgttggt tcccttattg atgcaacaat tgaacaatcc     360
tatgatgaag agtttattaa tgaagatatt gtaaatttgc ccgagaatgt cgattggaga    420
aaaaaaggag ctgtcactcc cgtaagacat cagggttcat gcggtagttg ttgggcattc    480
tcggccgttg caactgtaga gggaataaat aagattagaa ctggaaaatt agtagaatta    540
tcagagcaag aacttgttga ctgtgaaaga cgtagccatg ggtgcaaagg aggttatccg    600
ccgtatgcac ttgaatatgt ggctaagaat ggtattcact tgagatcaaa gtacccatat    660
aaagcaaagc aagggacttg tcgagccaaa caagtgggag gtccgattgt gaaaacttct    720
ggggttggac gtgtgcaacc aaataatgaa gggaatctct taaatgcaat tgcaaagcaa    780
cctgtgagcg ttgtggttga atccaaggga agacctttcc aattgtataa aggggggaata   840 tttgaggggc catgcggaac caaagtagat catgcagtaa cagcagttgg ttatggaaaa    900
agtggaggca aaggttacat actcatcaag aattcatggg gtactgcatg gggtgagaaa    960
ggatatataa gaatcaaaag agcccctgga aactccccag gagtgtgtgg actttataaa   1020
agctcatact atcctattaa aaatagagat aatggacgga tccagatccg cccatcatct  1080
caacacctca caagccatga atgaagctga                                   1110
```

<210> SEQ ID NO 9
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 9

```
Gln Asn Pro Ser Gln Gln Gln Pro Gln
1               5
```

<210> SEQ ID NO 10
<211> LENGTH: 12
<212> TYPE: PRT
<213> ORGANISM: Artificial sequence
<220> FEATURE:
<223> OTHER INFORMATION: Synthetic polypeptide

```
<400> SEQUENCE: 10

Arg Pro Gln Gln Pro Tyr Pro Gln Pro Gln Pro Gln
1               5                   10

<210> SEQ ID NO 11
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 11

Leu Gly Gln Gln Gln Pro Phe Pro Pro Gln Gln Pro Tyr
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 12

Pro Gln Pro Gln Pro Phe Pro Ser Gln Gln Pro Tyr
1               5                   10

<210> SEQ ID NO 13
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 13

Leu Gly Gln Gly Ser Phe Arg Pro Ser Gln Gln Asn
1               5                   10
```